United States Patent [19]
Gibson

[11] Patent Number: 5,847,221
[45] Date of Patent: Dec. 8, 1998

[54] METHOD FOR DECOLORIZATION OF ALKANOLAMINES AND ALKYLENEAMINES

[75] Inventor: Charles Arnold Gibson, South Charleston, W. Va.

[73] Assignee: Union Carbide Chemicals & Plastics Technology Corporation, Danbury, Conn.

[21] Appl. No.: 83,987

[22] Filed: Jun. 28, 1993

[51] Int. Cl.[6] .................................................. C07C 209/00
[52] U.S. Cl. ............................................ 564/498; 564/497
[58] Field of Search ..................... 564/497, 498, 564/503, 511, 512, 478, 479, 480, 469, 470

[56] References Cited

U.S. PATENT DOCUMENTS

| | | | |
|---|---|---|---|
| 2,744,938 | 5/1956 | Urban et al. | 260/613 |
| 3,131,132 | 4/1964 | Moss et al. | 203/35 |
| 3,207,790 | 9/1965 | Glew et al. | 260/584 |
| 3,453,183 | 7/1969 | Okubo | 203/33 |
| 3,723,529 | 3/1973 | Pitts et al. | 260/583 N |
| 3,819,710 | 6/1974 | Jordan | 260/584 R |
| 4,570,019 | 2/1986 | Gibson et al. | 564/498 |
| 4,731,165 | 3/1988 | Niebruegge et al. | 203/29 |
| 4,737,243 | 4/1988 | Siml et al. | 203/29 |
| 4,956,506 | 9/1990 | Latimer | 568/899 |

FOREIGN PATENT DOCUMENTS

| | | |
|---|---|---|
| 0477593 | 1/1992 | European Pat. Off. . |
| 1643277 | 5/1971 | Germany . |
| 1351050 | 12/1971 | United Kingdom . |
| 9322274 | 11/1993 | WIPO . |

OTHER PUBLICATIONS

Naflon® Product Bulletin from DuPont Chemical Co. Jul. 1986.

ACS Symposium Series 308, "Polymeric Reagents and Catalysts", W.T. Ford, 1985, pp. 42–67.

*Primary Examiner*—Brian M. Burn
*Attorney, Agent, or Firm*—S. H. Fiegedus

[57] ABSTRACT

Color-containing alkanolamines or alkyleneamines, having color numbers of up to 100 PtCo or higher, can be treated with polymeric solid acidic catalysts at elevated temperatures. Perfluorinated ion-exchange polymers in the acid form may be used as the polymeric solid acidic catalyst. In the presence of added water, these polymeric solid acidic catalysts produce decolorized alkanolamines or alkyleneamines having color numbers of 20 PtCo or less. The process of decolorization can be carried out in batch or continuous mode processes thus providing low cost, high quality and high purity end products.

6 Claims, No Drawings

METHOD FOR DECOLORIZATION OF ALKANOLAMINES AND ALKYLENEAMINES

BACKGROUND OF THE INVENTION

The present invention relates to processes for decolorizing alkanolamines and alkyleneamines, and more particularly, to both batch and continuous processes for producing alkanolamines and alkyleneamines having improved color characteristics by treatment with polymeric solid acidic catalyst.

Price and purity are important characteristics of a chemical's marketability to a potential customer. During industrial processes used to produce various chemicals, impurities often enter the processes and manifest themselves in the form of color contamination. The sources of this color contamination may be metals and metal compounds from the catalysts or equipment used in the processes, or conjugated organic compounds which are formed during the processes. Since the mechanism by which these color contaminants are formed varies from process to process, the decolorization process normally acts by a mechanism which depends on the color source.

It is well known that alkyleneamines, particularly the higher polyamines, become discolored during their preparation which generally reduces their commercial value. Various procedures have been used commercially or suggested for decolorizing or otherwise improving the color of these compounds including, for example, treating with hydrogen chloride or amine hydrochlorides as disclosed in JA-119902, UK Pat. No. 1,351,050; treatment with activated carbon, acid treated clays or acidic zeolites at elevated temperatures (about 200° C.) as disclosed in U.S. Pat. Nos. 3,723,529 and 4,737,243; and treatment with a powdered form of a sulfonic acid ion exchange resin as disclosed in U.S. Pat. No. 4,731,165. In each of these procedures, distillation is generally a final step needed to achieve the desired color, and neutralization of residues, handling and disposal of acids add additional process steps. In the several of the methods, recovery of the catalyst and/or reactivation of the catalyst are also additional process steps which complicate the processes.

U.S. Pat. No. 4,570,019 discloses a process which may be run continuously for producing polyalkylene polyamines having improved color characteristics which comprises treating discolored polyethylene polyamines with polyethylene polyamine hydrochloride in the presence of water at elevated temperatures, thus eliminating extra handling steps described in the processes above.

However, as is known in the art, methods used for decolorization of higher polyethylene polyamines are generally not transferable to compounds such as alkanolamines which are prepared by different processes and which use different reactants.

For example, alkanolamines may be conventionally prepared by reacting an alkylene oxide with ammonia or an amine, or, more particularly, alkanolamines such as aminoethylethanolamine may typically be prepared by the reductive amination of monoethanolamine.

Alkanolamines produced by these conventional processes can vary in color from nearly colorless water-white liquids to pale yellow. Alkanolamines, particularly ethanolamines, are susceptible to color formation in the presence of oxygen (e.g. from air leaks during manufacture and/or storage), excessive temperature and soluble metals such as iron or nickel. Also, impurities in raw materials may contribute to the initial and continuing formation of color bodies.

Various attempts to overcome the problems associated with color and color instability of alkanolamines have proven to be cost intensive and environmentally unacceptable. Such attempts have included purification by fractional distillation, concentration of color forming bodies or their precursors by fractional distillation, carbon treatment, the use of adsorbent materials, various hydrogenation techniques, and the use of reducing agents such as sodium borohydride and hydrazine.

U.S. Pat. No. 2,744,938 describes a process for the treatment of color-sensitive organic compounds which have become discolored through oxidation or upon aging. The patent specifically describes the method of removal of color bodies from alkylphenols with a catalyst-free solid adsorbent in the presence of hydrogen maintained at super atmospheric pressure. The thus treated alkylphenol is then separated from the solid adsorbent material.

U.S. Pat. No. 3,207,790 describes a process for improving the color of alkanolamines that develop undesirable color on aging by adding a sufficient amount of a borohydride of an alkali metal. The borohydrides have appreciable solubility in the alkanolamines and after dissolution, may remain in the solution or the alkanolamines may be distilled under reduced pressure.

U.S. Pat. No. 3,453,183 describes a method of removing aldehyde impurities from ethanolamines by forming a mixture of the ethanolamines with either powdered silicas, powdered silicates, liquid silicates or powdered aluminas, followed by separation of the ethanolamines by vacuum distillation.

U.S. Pat. No. 3,819,710 describes a process for improving color and color stability of ethanolamines by hydrogenation using selected catalysts and selected catalysts conditions. Useful catalysts for the process include Raney nickel, platinum, palladium or ruthenium.

EP 0477593 describes purification and decolorization of off-color crude N-dialkyl dialkanolamines by vacuum distilling in the presence of water and a water-soluble metal borohydride.

The above patents confirm the need for methods of improving the color characteristics of both alkanolamines and alkyleneamines. While some of the processes such as the use of solid adsorbents results in improved color, such processes are not entirely suitable for large scale decolorization and require labor intensive steps for recovery of the desired product adding expense to the process in terms of time of treatment, equipment costs, and disposal of byproducts.

Other methods, such as hydrogenation of color impurities requires expensive Raney nickel which must be replaced on a regular schedule. Hydrogenation systems also require special equipment for hydrogen supply, mixing and, after reduction, filtration to remove the Raney nickel, since distillation in the presence of Raney nickel tends to generate color and deactivate the catalyst.

The need exists for an inexpensive easily operated process of producing alkanolamines or alkyleneamines having reduced color.

SUMMARY OF THE INVENTION

In accordance with the present invention there is provided a method of producing alkanolamines or alkyleneamines having reduced color comprising contacting color-containing alkanolamines or alkyleneamines with polymeric solid acidic catalysts in the presence of added water at an elevated temperature, for a time sufficient to reduce the color of the alkanolamines or alkyleneamines. Preferably the decolorization step is carried out under pressures high enough to maintain water in the liquid phase.

The heterogeneous catalysts used in accordance with the present invention, advantageously provide versatility in allowing both batch and continuous processing of the color-containing alkanolamines and alkyleneamines. The processes may readily be incorporated into typical manufacturing facilities, providing low cost, high quality and high purity end products.

The methods of the invention may effectively treat color-containing alkanolamines and alkyleneamines with colors up to a Platinum-Cobalt (PtCo) number of 100 or higher to obtain products with reduced color numbers of about 20 PtCo or less.

DESCRIPTION OF THE PREFERRED EMBODIMENTS

The discolored alkanolamines or alkyleneamines to which the present invention relates can be prepared by any of the processes well known in the art such as where a crude mixture is produced and then subjected to refining procedures where desired individual components or mixtures thereof are separated and recovered. The products recovered by the various refining or separation processes are, in general, discolored, having PtCo numbers ranging from up to 700 or greater, as determined using ASTM Method 1209 "Color of Clear Liquids (Platinum-Cobalt Scale)."

In the absence of any pre-treatment, refined alkanolamines, such as for example aminoethylethanolamine (AEEA), may have color numbers being close to about 60 PtCo or higher.

In addition, alkanolamines or alkyleneamines which may have been treated previously by other known decolorization methods, some of which may have lower color numbers initially, upon storage become discolored due to increases in storage temperatures.

The following description of the preferred embodiments will refer to decolorization of alkanolamines, in particular AEEA. However, the scope is intended to include both alkanolamines and alkyleneamines, as it has been surprisingly found that the present invention may be applicable to both types of compounds when water is added, and at elevated temperatures.

Color impurities found in alkanolamines may be removed by contacting color-containing alkanolamines with polymeric solid acidic catalysts. A preferred class of polymeric solid acidic catalysts include perfluorinated ion-exchange polymers (PFIEP) such as Nafion®, a registered trademark of DuPont Chemical Company for copolymers of tetrafluoroethylene and perfluorinated monomers. Nafion® is prepared from a copolymer of tetrafluoroethene and perfluoro-2-(fluorosulfonlyethoxy)-propyl vinyl ether. The perfluorinated vinyl ether is produced by reaction tetrafluoroethene with $SO_3$ to form a cyclic sultone which subsequently rearranges to fluorocarbonylmethane-sulfonyl fluoride. The linear analog reacts with two moles of fluoropropylene oxide to yield a compound with a terminal 1-fluorocarbonyltrifluoroethoxy group. This group loses carbonyl fluoride on heating with $Na_2CO_3$ to give the perfluorinated vinyl ether. The copolymer resin in the sulfonyl fluoride form is base hydrolyzed to the alkali form and then acidified to the sulfonic acid form.

Polymeric solid acidic catalysts may be purchased in the acid form, such as Nafion®-H or Nafion®-NR50 available from Aldrich Chemical Company. In the acidic form, these materials are composed of sulfonic acid groups adjacent to fluorinated carbon in a perfluorinated polymer backbone. The polymeric solid acidic catalyst may be used alone or may be coated onto a support material such as silicas, aluminas, porous glass beads, ceramics and the like using methods known in the art such as impregnation. The surface area and pore diameters of these supports can vary and are not critical to the operation of the polymeric solid acidic catalyst.

When treating color-containing alkanolamines or alkyleneamines, the amount of catalyst used depends on the concentration and strength of the acid functionality. The acid concentration and strength of the polymeric solid acidic catalyst may be determined by methods known in the art such as non-aqueous amine titration (Hammett indicator) and the like. Generally, from about 0.5 to 10 percent by weight of the polymeric solid acidic catalyst is used based on the weight of material to be treated. For example, when using Nafion®, the amount of catalyst used is preferably 1 to 5 percent by weight of the material to be treated.

Without intending to be bound by any particular theory, it is believed that in the presence of added water, polymeric solid acidic catalysts such as Nafion®, after an initial weight loss, are stabilized, resulting in better performance without the need for continuous regeneration of the catalyst. The amount of water present is generally in the range of 1 to 10 percent, preferably 3 to 8 percent and most preferably 4 to 6 percent by weight of the material to be decolorized.

The above described polymeric solid acidic catalysts may reduce color during initial use without water, however, the degree of color reduction, stability of the decolorized product and stability of the catalyst itself, is low and the process may not be adaptable for continuous use processes. Further, anhydrous operation at elevated temperature may result in excessive catalyst weight loss and degradation of the catalyst due to the accumulation of heavy byproducts which may form during the color removal step.

The process may be run over a wide ranges of temperatures from about 150° to 230° C. Preferably, the temperature range is from about 201° to 215° C., and most preferably from about 205° to about 210° C. The pressure of the system should be high enough to assure retention of water in the liquid phase, and is normally in the range of 1–100 psig, more preferably 20–75 psig, and most preferably 50–65 psig.

In a typical embodiment, the process of the present invention may be carried out in both batch and continuous modes. In the batch mode, treated product is discharged and fresh product, to be treated, is added. The catalyst may conveniently be maintained in the reactor by use of a basket made of porous screens. In a batch mode operation, the use of agitation may be beneficial in improving catalyst efficiency. Typical means of agitation include the use of mechanical stirrers at speeds ranging from about 400 to about 1200 rpm.

In a continuous mode of operation, a fixed catalyst bed may be used and product to be treated pumped through the bed. In such a continuous process, water is typically introduced as makeup and normal distillation is used to provide low color and color stable products. Although the mechanism of decolorization is not completely understood, it is believed that during a continuous process, color formers are destroyed during the process and become light fragments which are removed during distillation or heavy fragments which go out with the residue stream.

The color-containing alkanolamines or alkyleneamines should be in contact with the polymeric solid acidic catalyst for a time sufficient to produce a decolorized product. Typically, the residence time for either the batch or continuous mode of operation may be up to about 8 hours, preferably about 4 to 6, and most preferably about 4 to 5 hours. The length of time for decolorization depends on the amount of polymeric acidic catalyst present in the treatment vessel, temperature, and amount of water present in the system as illustrated by the following examples.

EXAMPLES

Although Nafion® has been used in the decolorization of alkyleneamines (U.S. Pat. No. 4,731,165), the patent does not discuss that addition of water to the process and states that Nafion's temperature stability places an effective ceiling of 200° C. on the process. It would further be unexpected that a process for decolorization of alkyleneamines could be transferred to alkanolamines due to differences in manufacturing and refining processes which result in the formation of color-forming bodies.

The following examples demonstrate the effectiveness of polymeric solid acid catalysts in the color reduction of alkanolamines. The solid acidic catalyst used was Nafion® in acidic form purchased from DuPont Chemical Company.

Crude AEEA having an initial PtCo number of 79.5 was used for the decolorization process. The distillation equipment consisted of a 5 tray Oldershaw column having one inch tray spacings, equipped with a distillation head.

Example 1

Control

Crude AEEA, 250 grams, is mixed with 10 grams of distilled deionized water. The mixture is charged to the distillation equipment and heated to 205°–210° C. for three hours at a pressure of 0.7 psig. The pressure is reduced to 2 mm Hg and a first distillate fraction removed. A second distillate fraction, 200 grams of untreated AEEA, is removed at a head temperature of 105° C., 2.8 mm Hg, and has a color of 53 PtCo.

Example 2

Color Reduction Using Nafion®

Crude AEEA, 300 grams and 12 grams of distilled, deionized water are charged to the distillation equipment described above containing Nafion® tubing (3 grams, ⅛ inch by ½ inch sections). The materials are heated to 205°–210° C. for 3 hours. The reactants are cooled to ambient temperature and the supernatant liquid transferred to the distillation equipment. A first distillate fraction is removed at 84° C., 0.7 mm Hg. The second distillate fraction, 212 grams of treated AEEA, is removed under the same conditions and has a color number of 9.7 PtCo.

Example 3

Comparative Example

Temperature effect on performance of Nafion® was evaluated by treating crude AEEA, having an initial PtCo number of 79.5, at 150° C. and 180° C. The results are shown in the following table and as compared to Example 2:

TABLE 1

| Temperature Effect on Decolorization of AEEA Using Nafion ® | |
|---|---|
| Temperature | PtCo Number |
| 150° C. | 38.8 |
| 180° C. | 21.4 |
| 205–210° C. (Ex. 2) | 9.7 |

What is claimed is:

1. A method of producing alkanolamines or alkyleneamines having a reduced color comprising contacting, in the presence of about 1 to about 10% by weight of the material to be decolorized of added water, maintained in the liquid phase at a temperature of 201° to about 230° C. and a pressure of about 1 to about 100 psig, color-containing alkanolamines or alkyleneamines with a polymeric solid acidic catalyst to reduce the color of said alkanolamines or alkyleneamines.

2. The method of claim 1 wherein said polymeric solid acidic catalyst is a perfluorinated ion-exchange polymer in the acid form.

3. The method of claim 2 wherein the perfluorinated ion-exchange polymer in acid form is a copolymer of tetrafluoroethylene and perfluorinated monomers having sulfonic acid groups.

4. The method of claim 1 wherein said polymeric solid acidic catalyst is present in a concentration ranging from about 0.5 to 10 percent by weight of said alkanolamine or alkyleneamine.

5. The method of claim 1 wherein said polymeric solid acidic catalyst is present in a concentration ranging from about 1 to 5 percent by weight of said alkanolamine or alkyleneamine.

6. The method of claim 1 wherein water is added at a concentration of from about 4 to about 6 percent by weight of the alkanolamine or alkyleneamine.

* * * * *